United States Patent [19]

Takahashi et al.

[11] Patent Number: 4,591,249
[45] Date of Patent: May 27, 1986

[54] EXPOSURE CONTROL SYSTEM FOR OPHTHALMIC PHOTOGRAPHING APPARATUS

[75] Inventors: Susumu Takahashi; Kiwami Horiguchi, both of Tokyo, Japan

[73] Assignee: Tokyo Kagaku Kikai Kabushiki Kaisha, Tokyo, Japan

[21] Appl. No.: 656,149

[22] Filed: Sep. 28, 1984

[30] Foreign Application Priority Data

Oct. 4, 1983 [JP] Japan .................................. 58-185702

[51] Int. Cl.⁴ ............................................. G03B 29/00
[52] U.S. Cl. ..................................................... 354/62
[58] Field of Search .............................. 354/62; 351/7

[56] References Cited

U.S. PATENT DOCUMENTS

| 4,149,787 | 4/1979 | Kobayashi et al. | 354/62 |
| 4,253,744 | 3/1981 | Sawa . | |
| 4,400,070 | 8/1983 | Isono et al. | 354/62 |
| 4,412,728 | 11/1983 | Sakane et al. | 354/62 |
| 4,429,970 | 2/1984 | Fujiwara . | |
| 4,436,388 | 3/1984 | Takahashi et al. | 354/62 |
| 4,452,517 | 6/1984 | Kohayakawa | 354/62 |
| 4,469,416 | 9/1984 | Isono | 354/62 |

Primary Examiner—Russell E. Adams
Attorney, Agent, or Firm—Brumbaugh, Graves, Donohue & Raymond

[57] ABSTRACT

Exposure control system for ophthalmic photographing apparatus including a focusing mark projecting optical system for projecting focusing mark on a patient's eye so that the focusing condition can be clearly recognized. A detector is provided for detecting the intensity of the light from the mark image. The signal from the detector is used to control the exposure control system by for example determining the time in which the photographing light source is energized.

12 Claims, 14 Drawing Figures

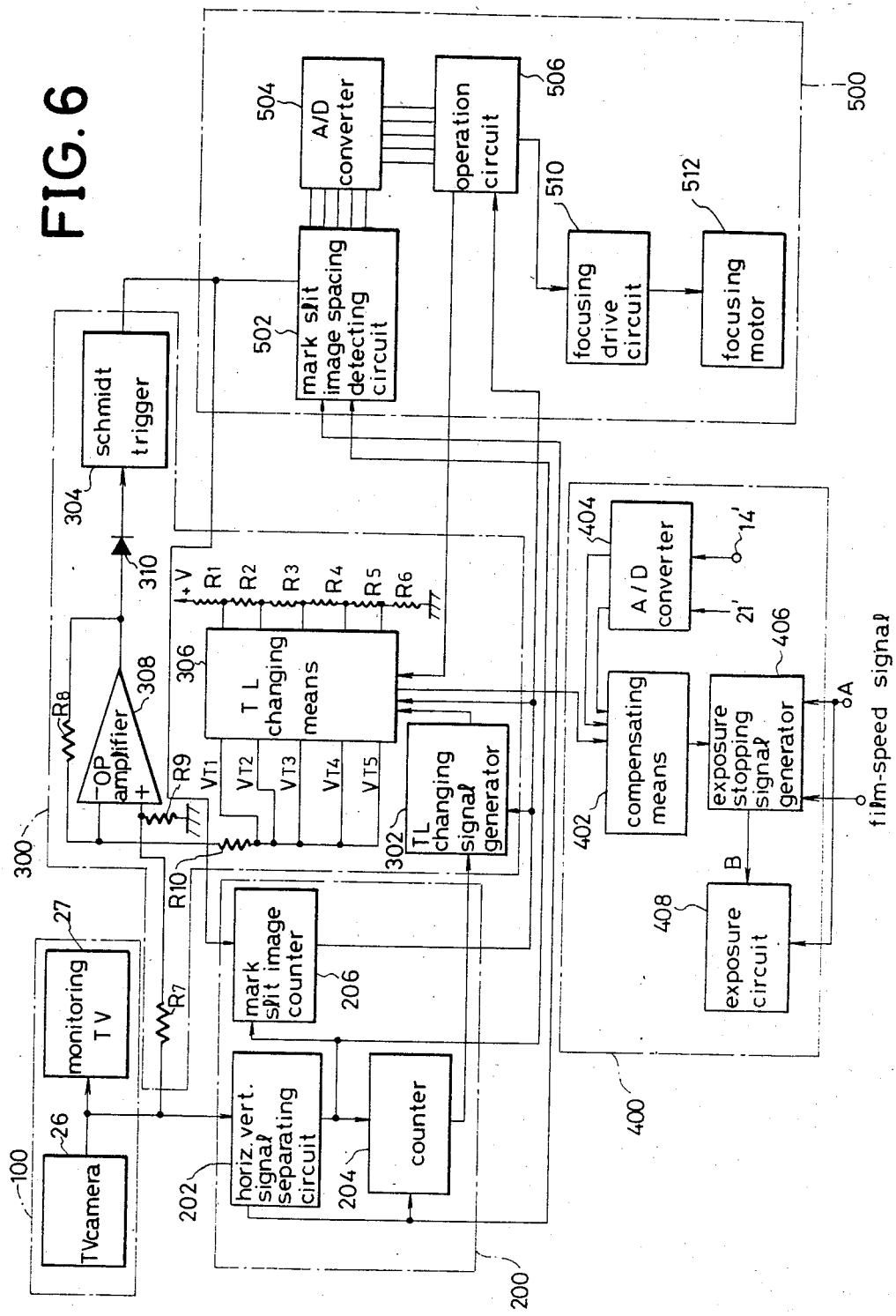

EXPOSURE CONTROL SYSTEM FOR OPHTHALMIC PHOTOGRAPHING APPARATUS

BACKGROUND OF THE INVENTION

1. Field of the Invention

The present invention relates to an ophthalmic photographing apparatus and more particularly to an exposure control system therefor. More specifically, the present invention pertains to an exposure control system for an ophthalmic photographing apparatus wherein the exposure is determined in accordance with the intensity of light reflected at the brightest part of an ophthalmic subject to be photographed, for example, a portion where focusing mark images are projected.

2. Description of Prior Art

In a conventional ophthalmic photographing instrument for example, an eye fundus camera, the exposure for photographing is generally determined by detecting the overall quantity of light reflected at the retina of a patient's eye by means, for example, a CdS detector. In other words, the exposure is determined in accordance with the average quantity of light reflected by the retina. It should however be noted that the intensity of the light reflected at the retina is not sufficient to precisely control the exposure since the reflectivity of the retina is very low.

On the other hand, the non-mydriatic eye fundus camera in which the retina is illuminated by an infrared beam for observation and focusing has recently come into wide use because it does not require projected administration of mydriatic to the pupil. With the non-mydriatic eye fundus camera, however, it is almost impossible to grasp the focus condition of the subject from the retina image on a monitoring TV since only a rough image can be produced on the TV. Therefore, an eye fundus camera is usually provided with a focusing mark projecting system for projecting images of a plurality of focusing marks on the retina through beams of infrared rays which are brighter than the background so that the operator can grasp the focus condition from the images of the focusing marks. It should therefore be noted that if exposure control is made based on the light reflected at the retina, the control is effected by the brighter light from the focusing mark images so that an accurate exposure control cannot be performed.

DESCRIPTION OF THE INVENTION

Object of the Invention

It is an object of the present invention to provide an exposure control system in ophthalmic photographing for determining exposure in accordance with the intensity of light reflected at the portion of the subject which is illuminated by a high intensity light.

Another object of the present invention is to provide an exposure control system for ophthalmic photographing which can carry out an accurate control even when a subject to be photographed is illuminated at a part by a brighted light than other parts.

A further object of the present invention is to provide an ophthalmic photographing apparatus having a focusing system which carries out focusing in accordance with the positional relation among a plurality of focusing mark images and an exposure control system which determines the appropriate exposure in accordance with the light intensity of the focusing mark images.

SUMMARY OF THE INVENTION

According to the present invention, the above and other objects can be accomplished by an ophthalmic photographing apparatus comprising an illuminating optical system for projecting beams of illuminating light to a subject to be photographed, a mark projecting optical system for projecting a mark on the subject by a mark projecting light, a photographing optical system including a photographing film plane and optical means for producing an image of the subject on the film plane, photodetecting means for detecting a light which is a reflection of the mark projecting light at the retina to produce a mark signal, exposure control means including photographing light source means and means for controlling the light source means in accordance with the mark signal to control exposure in photographing.

In one mode of the present invention, the mark may be a focusing mark and the mark projecting system includes means for projecting the focusing mark on the subject with a brightness greater than that of background. The illuminating system may project an observing light and the apparatus may include an observing optical system for observing the subject under the illuminating light from the illuminating system.

The above and other objects and features of the present invention will become apparent from the following descriptions of preferred embodiments taking reference to the accompany drawings.

BRIEF DESCRIPTION OF THE DRAWINGS

FIG. 6 is a circuit diagram of an electric system including a focusing circuit and an exposure control circuit in accordance with one embodiment of the present invention;

DESCRIPTION OF THE PREFERRED EMBODIMENT

Figure 1:
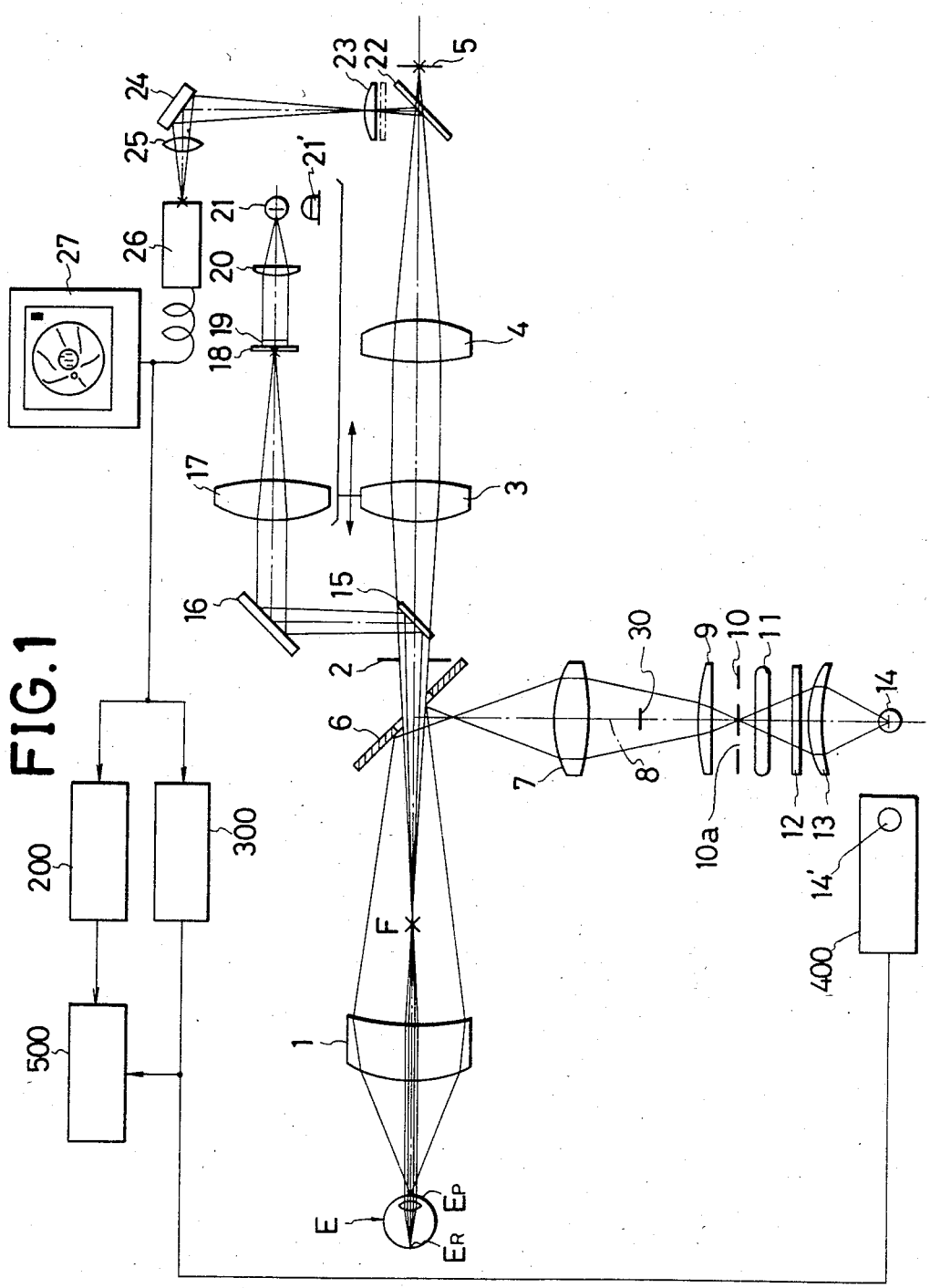
FIG. 1 is a diagrammatic illustration of the optical system of an eye fundus camera in which the present invention can be embodied.

Referring now to the drawings, there is shown a non-mydriatic eye fundus camera which includes an optical system, and an exposure and focusing system.

In FIG. 1, there is shown the optical system of an eye fundus camera which includes an observing and photographing optical system comprising an objective lens 1 adapted to be placed opposite to a patient's eye E. On the optical axis of the objective lens 1, there is an aperture plate 2 located conjugate with the pupil $E_p$ of the patient's eye E with respect to the objective lens 1. The photographing optical system further includes a focusing lens 3, an imaging lens 4 and a photographing film 5 which are arranged in this order along the optical axis of the objective lens 1. Although not shown in FIG. 1, there is provided a shutter in front of the film 5. The lenses 3 and 4 are arranged so as to form an afocal optical system. In the photographing optical system, an image of the retina $E_R$ of the patient's eye E is once produced at the point F and then at the film 5.

In front of the film 5, there is obliquely provided a retractable mirror 22. Along the reflecting optical path of the mirror 22, there is a field lens 23 which has an image plane substantially conjugate with the photographing film 5. The light beam which has passed through the imaging lens 4 is therefore reflected by the mirror 22 to produce an image of the retina $E_R$ on the field lens 23. The image is then relayed through a mirror 24 and an imaging lens 25 to the image pickup tube of a TV camera 26 which produces a signal for producing a visible image on a monitoring TV 27. The arrangements constitute on observing system.

The eye fundus camera further includes an illuminating optical system which incudes an observation light source 14 and a photographing light source 11. Between the observation light source 14 and the photographing light source 11, there is located a condenser lens 13 and a heat-blocking filter 12. The light source 14 produces beams of infrared ray for observation purpose. The light from the light source 11 or 14 is passed through a ring-shaped aperture 10a of an aperture plate 10, then through a condenser lens 9 and a relay lens 7 aong the illuminating optical axis 8 which intersects the optical axis of the objective lens 1. On the optical axis of the objective lens 1, there is obliquely provided an apertured mirror 6 which is substantially conjugate with the pupil $E_p$ of the patient's eye E. The illuminating light which has passed through the aperture 10a produces an image of the aperture 10a on the reflective surface of the mirror 6 and is reflected toward the patient's eye E to form an image of the aperture 10a in the pupil $E_p$ and then illuminate the retina $E_R$. The light source 14 is of a variable intensity type so that it can illuminate the retina $E_R$ with a desired brightness to thereby make it possible to observe the image of the retina $E_R$ on the TV 27 with an appropriate contrast.

The eye fundus camera further includes a mark projecting optical system for the purpose of focusing. The system includes a light source 21 and a condenser lens 20 which define a mark projecting optical path. In the mark projecting optical path, there is a mark plate 18 combined with light deflecting prisms 19. The light which has passed through the mark plate 18 is passed through a relay lens 17, reflected by mirrors 16 and 15 to proceed through the aperture plate 2 and the aperture in the apertured mirror 6 to the objective lens 1. The mark projecting light is then passed through the objective lens 1 and the pupil $E_R$ of the patient's eye E to the retina $E_R$.

Figure 2A:
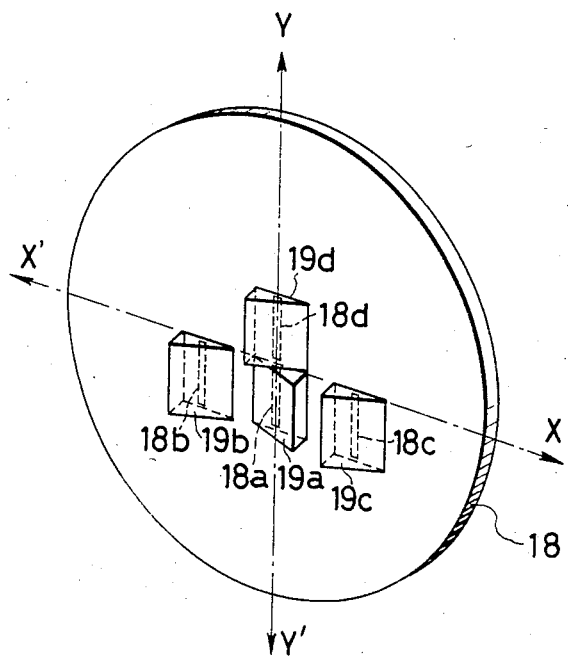
FIG. 2(a) is a perspective view of a mark plate adopted in the mark projecting system of the eye fundus camera.
Figure 2B:
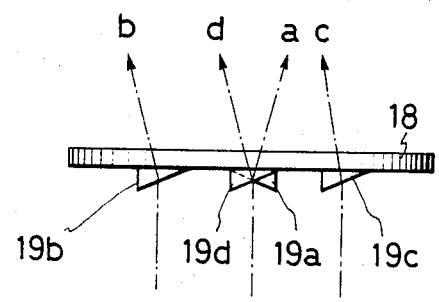
FIG. 2(b) is a top plan view of the mark plate showing the paths of mark projecting light beams.

Referring to FIG. 2(a), it will be noted that the mark plate 18 has a mark comprised of a pair of slits 18a and 18d aligned along a vertical line Y-Y' and a further pair of slits 18b and 18c which are parallel with the slits 18a and 18d but spaced from the vertical line Y-Y' by the same distance in the opposite directions. The deflecting prisms include prisms 19a, 19b, 19c and 19d which are associated respectively with the slits 18a, 18b, and 18c and 18d. The prisms 19a, 19b, 19c and 19d function to deflect the light beams passing through the slits 18a, 18b, 18c and 18d in the directions shown by arrows a, b, c and d, respectively, as shown in FIG. 2(b). As described previously, the light beams which have passed through the slits 18a, 18b, 18c and 18d in the mark plate 18 are passed through the relay lens 17 and then reflected by the mirrors 16 and 15. The light beams then pass through the aperture plate 2 and the aperture in the mirror 6 to form images of the slits at the position F. The slit images are then relayed through the objective lens 1 and the pupil $E_p$ of the eye E to the retina $E_R$.

Figure 3:
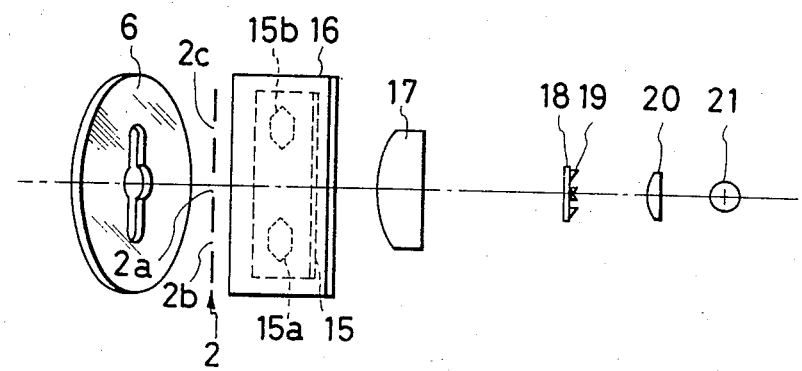
FIG. 3 shows an example of the mark projecting system.

The mark projecting beams are divided in two directions as described above referring to FIG. 2(b). In order to reflect these beams toward the objective lens 1, the mirror 15 has a pair of reflective surfaces 15a and 15b which are positioned symmetrically with respect to the optical axis of the objective lens 1 (FIG. 3). With this structure of the mirror 15, the mirror 15 does not disturb the light which has emitted from the eye retina $E_R$ and passed through the objective lens 1 to the observing optical system. As shown in FIG. 3, the aperture plate 2 has a central aperture 2a for passing the observing lightbeam and a pair of apertures 2b and 2c for passing the mark projecting light beams. It will also be seen in FIG. 3 that the apertue of the mirror 6 is of a sidewardly elongated configuration.

In order to increase the contrast of the mark image at the retina, it is desirable to block the background illumination at the area where the mark image is projected. For this purpose, the illustrated eye fundus camera includes a retractable opaque plate 30 in the illuminating optical system. The plate 30 is located substantially conjugate with the retina $E_R$ of the patient's eye E and has a diameter sufficient to cover the mark image.

In the optical system shown in FIG. 1, the relay lens 17, the mark plate 18, the deflecting prisms 19, the condenser lens 20 and the light source 21 of the mark projecting system are asssembled so that they are moved as a unit along the projecting optical axis and the assembly is interconnected with the focus lens 3 in the observing optical system so that they move together. Thus, the focus condition of the observing optical system can be judged by the focus condition of the projected mark image.

Figure 4:
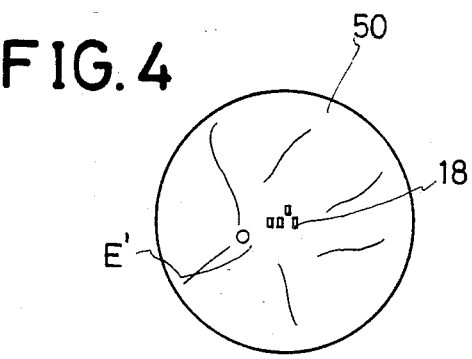
FIG. 4 shows an image of the eye fundus as produced on a monitoring TV.
Figures 5A, 5B, 5C:
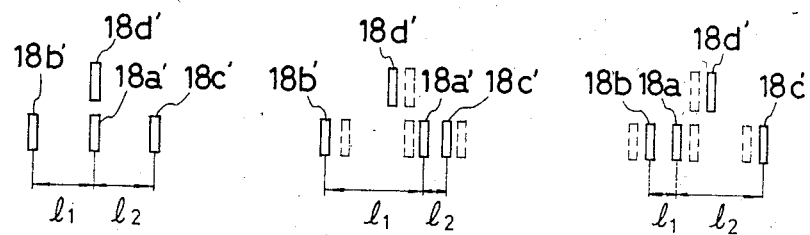
FIGS. 5(a), (b) and (c) show mark images under different focus conditions.

With the arrangement described above, there is displayed on the monitoring TV 27 an image 50 of the retina $E_R$ with an image 18' of the mark superposed thereon as shown in FIG. 4. The relationship between the focus condition and the position of the mark image is shown in FIG. 5. In FIG. 5(a), there are shown images 18a', 18b', 18c', and 18d' of the mark slits 18a, 18b, 18c and 18d in the focused condition. FIGS. 5(b) and (c) show the images under out-of-focus conditions. In FIGS. 5(b) and (c), the locations of the mark slit images in focused condition are shown by dotted lines for reference. Where the focal plane of the mark slit images of offset from the retina $E_R$ in the direction of the optical axis of the objective lens 1, the mark slit image 18a' is displaced in a direction opposite to the direction of displacement of the mark slit images 18b', 18c' and 18d'. Under a focused condition, the spacing l1 between the slit images 18a' and 18b' is equal to that l2 between the slit images 18a' and 18c'. It will therefore be understood that, by detecting the spacings l1 and l2 as electric signals, it becomes possible to know the focus condition of the observing and photographing optical system.

Referring now to FIG. 6, there is shown an electric circuit for the exposure control and focusing system for processing electric signals which are produced by the TV camera 26 from the images of the retina $E_R$ and the mark slits. The circuit includes an image forming section 100, a timing signal section 200, a mark slit image signal detecting section 300, an exposure control section 400, and a focusing control section 500.

Figure 7:
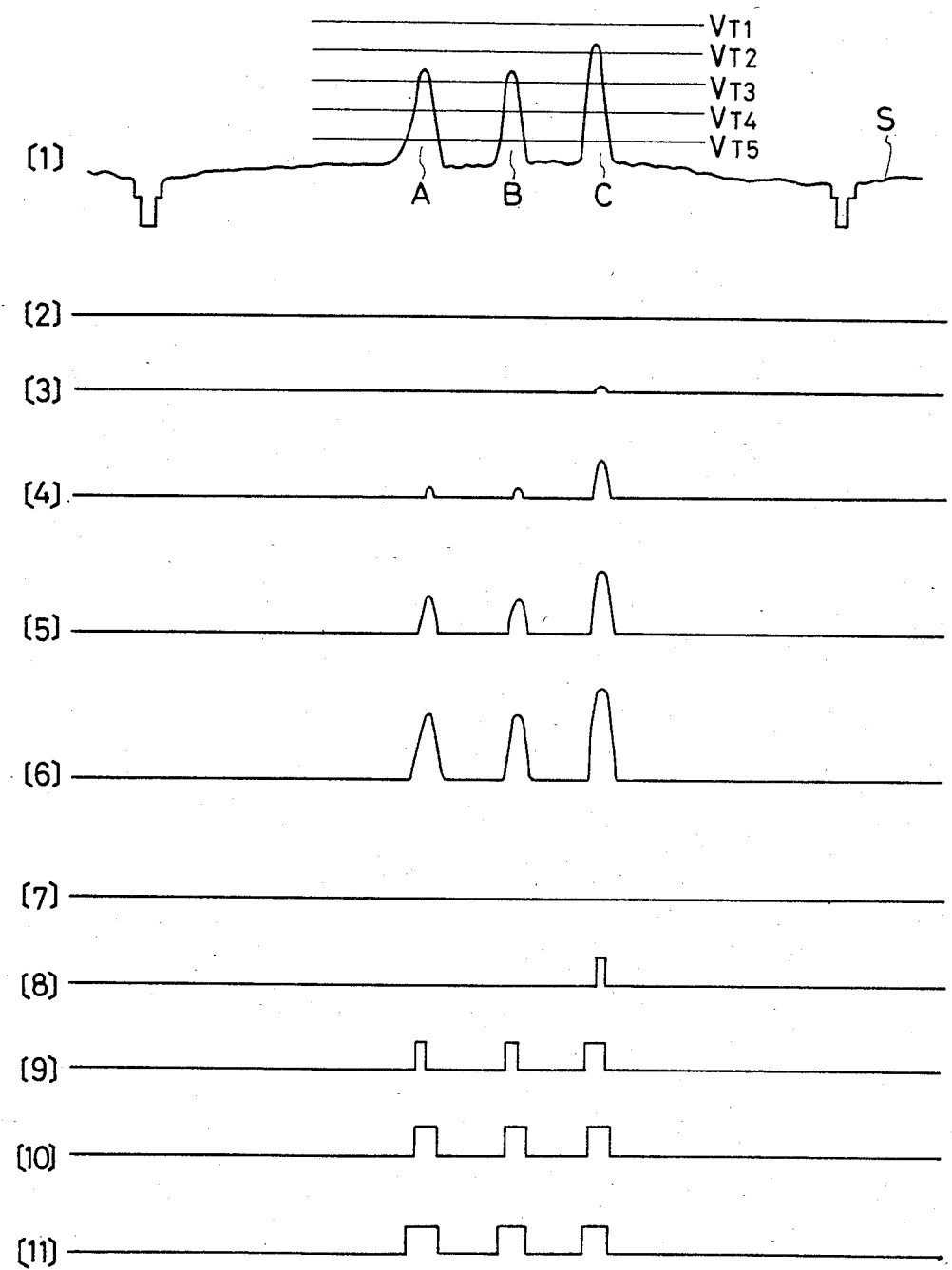
FIG. 7 shows signal wave patterns produced in the circuit shown in FIG. 6.

The image forming section 100 is comprised of the TV camera 26 and the monitoring TV 27 which produce the image signals S of the retina $E_R$ superposed with the images 18' of the mark slits as shown in FIG. 7.

The timing signal section 200 includes a horizontal and vertical synchronous signal separating circuit 202, a main counter 204, and a mark slit image counter 206. The separating circuit 202 has an input connecting with the TV camera 26 to receive image signals therefrom and functions to separate horizontal sychronous signals from vertical synchronous signals. The counter 204 has an input connected with the separating circuit 202 and functions to count the horizontal synchronous signals, while the counter 204 is cleared by the vertical synchronous signals.

The counter 206 has an input connected with the counter 204 and a schmidt trigger 304 and functions to count the mark slit images, while the counter 206 is cleared by the horizontal synchronous signal. When the counter 206 has counted the predetermined number of mark slit images, it produces a pulse which is applied to a threshold level (hereinafter called TL) changing signal generator 302, a TL changing circuit 306, and an operation circuit 506.

The mark slit image signal detecting section 300 includes the TL changing signal generator 302 having an input connected with the counters 204 and 206 to function to produce a TL changing signal in accordance with the output of the counters 204 and 206 in a manner which will be described later.

The detecting section 300 further includes TL changing means 306 having an input connected with the mark slit image counter 206 and TL changing signal generator 302. The TL changing means 306 functions to select in accordance with the output of the signal generator 302 one of threshold levels $VT_1$ through $VT_5$ which are determined by resistors $R_1$ to $R_6$, and produces a digital output which is applied to a compensating means 402 upon receipt of the output of the counter 206 which is produced at the time when the counter 206 has counted the predetermined number of mark slit images. The digital output of the means 306 may be referred as the "mark signal". In the present embodiment, the threshold level VT selected by the TL changing means 306 is regarded as a value generally corresponding to the intensity of the light reflected at the portion of the retina $E_R$ where the mark slit image is projected.

The detecting section 300 further includes an OP amplifier 308, a diode 310, and a schmidt trigger 304. The OP amplifier 308 has a positive input connected with the TV camera 26 through a resistor $R_7$ and a negative input connected with the TL changing means 306. The OP amplifier 308 also has an output which is connected through a feedback resistor $R_8$ with the negative input. The amplifier 308 functions to amplify the image signal S from the TV camera 26. The OP amplifier 308 produces an output as shown in FIG. 7(1) which is a signal having a zero level of the output level $V_T$ of the TL changing means 306. Thus, when the output level $V_T$ is changes as shown by $V_{T1}$ through $V_{T5}$, the waveform of the image signal S is not changed, but its level is changed.

The diode 310 has an input connected with the OP amplifier 308 and functions to rectify the output of the OP amplifier 308. FIGS. 7(2) through 7(6) respectively show outputs of the OP amplifier 308 corresponding to the levels $V_{T1}$ through $V_{T5}$ of the outputs TL of the TL changing means 306.

The schmidt trigger 304 is connected with the diode 310 to convert the analogue signal outputs of the diode 310 into rectangular signals as shown in FIGS. 7(7) tnrough (11).

The exposure control section 400 includes a photoelectric element 14' located adjacent to the light source 14 to detect the intensity of the light emitted from the light source 14, a photoelectric element 21' located adjacent to the light source 21 in the mark projecting system to detect the intensity of light emitted from the light source 21, an A/D converter 404, a compensating means 402, an exposure stopping signal generator 406, and an exposure circuit 408.

The A/D converter 404 is connected with the photoelectric elements 14' and 21' and functions to convert the outputs of the elements 14' and 21' into digital signals M1 and M2, respectively. The compensating means 402 has an input connected with the TL changing means 306 and the A/D converter 404, and functions to modify the output TL of the means 306 in accordance with the outputs of the elements 14' for producing an output accurately representing the reflectivity of the retina. In modifying the output TL, calculations are carried out to obtain an output TL' of the compensating means 402 in accordance with the formula $$TL' = (M_3/M_2) - k_1, M_1$$

where: $M_3$ is the value of TL as obtained at the means 306, and $k_1$ is a constant.

The output TL' of the compensating means 402 is applied to the exposure stopping signal generator 406.

The signal generator 406 further receives a film-speed signal and a shutter release signal A and calculates the exposure time in accordance with the output of the compensating means 402 and the film-speed signal. The exposure time starts upon shutter release which is initiated by a depression of a shutter release button at which time, the photographing light source 11 is fired. The signal generator 406 produces an exposure stopping signal B upon expiry of the exposure time. The signal B is then applied to the exposure means 408.

Figure 8:
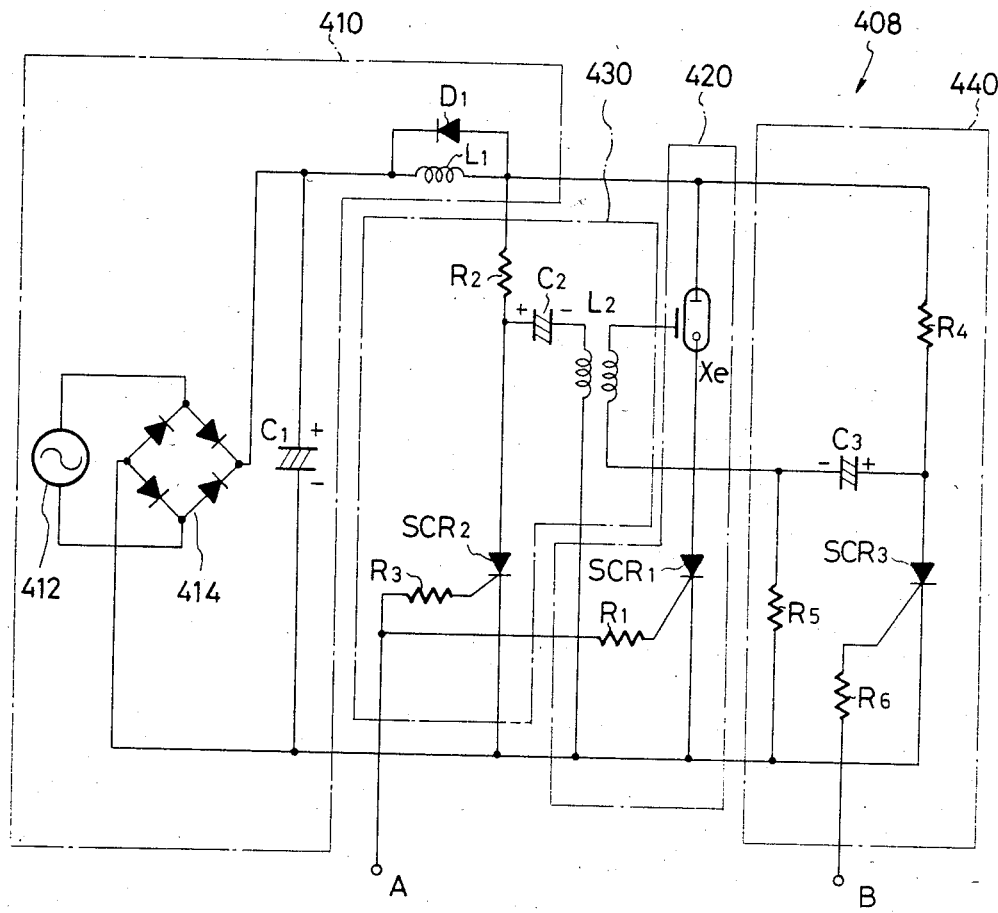
FIG. 8 is a circuit diagram of the exposure circuit shown in FIG. 6.

The exposure means 408 is shown in detail in FIG. 8. The exposure means 408 is provided for controlling the photographing light source 11, such as a xenon flash tube Xe in accordance with the shutter signal A and the exposure stopping signal B. The means 408 consists of a power section 410, a lighting section 420, a trigger section 430, and a current converting section 440.

The power section 410 includes a diode bridge 414 connected with a AC power unit 412, a main capacitor $C_1$ connected in parallel with the diode bridge 414, and a parallel circuit of a diode $D_1$ and a coil $L_1$ connected with the main capacitor $C_1$. AC voltage from the AC power unit 412 is converted into DC voltage by the diode bridge 414 and applied to the main capacitor $C_1$ to be charged therein. The DC voltage charged in the main capacitor $C_1$ is applied to the lighting section 420 and the current converting section 440 through the parallel circuit of the diode $D_1$ and the coil $L_1$.

The main capacitor $C_1$ supplies a current enough to fire the xenon flash tube Xe and its capacity depends on the amount of radiation of the tube Xe. The coil $L_1$ controls an instantaneous current and the diode $D_1$ prevents a back-rush of the current.

The lighting section 420 includes the aforementioned xenon flash tube Xe, a thyristor $SCR_1$ connected with the tube Xe in series, and a resistor $R_1$ connected with the gate of the thyristor $SCR_1$. The gate of the thyristor $SCR_1$ receives the shutter signal A through the resistor $R_1$. When the shutter release button is depressed, the thyristor $SCR_1$ turns "on" so that the voltage from the power section 410 is supplied to the tube Xe.

The trigger section 430 includes a coil $L_2$, a capacitor $C_2$ connected with the coil $L_2$, a resistor $R_2$ connected with the parallel circuit of the diode $D_1$ and the coil $L_1$, a thyristor $SCR_2$ connected with the resistor $R_2$ and the capacitor $C_2$, and a resistor $R_3$ connected with the gate of the thyristor $R_3$. One of the secondary terminals of the coil $L_2$ is connected with the trigger electrode of the tube Xe. The trigger section 430 functions to produce a high voltage for starting radiation of the tube Xe corresponding to the shutter signal A. Before the shutter signal A is supplied to the thyristors $SCR_1$ and $SCR_2$ through the resistors $R_1$ and $R_3$, the thyristor $SCR_2$ is "off" and the capacitor $C_2$ is charged in the polarity shown in FIG. 3 through the resistor $R_2$ and the coil $L_2$. After the shutter signal A is supplied to the thyristor $SCR_1$ and $SCR_2$ through the resistors $R_1$ and $R_3$, the thyristors $SCR_1$ and $SCR_2$ turn "on" so that a circuit is established across the capacitor $C_2$, and a current is produced through the primary winding of the coil $L_2$. Thus, a high voltage is produced in the secondary winding and applied to the trigger electrode and the cathode of the tube Xe. The tube Xe therefore starts to fire since the thyristor $SCR_1$ is already turned "on".

The current inverting section 440 includes a capacitor $C_3$, resistors $R_4$ and $R_5$ connected with the capacitor $C_3$, a thyristor $SCR_3$ connected with the resistor $R_2$ and the capacitor $C_3$, and a resistor $R_6$ connected with the gate of the thyristor $SCR_3$. The resistance value of the resistor $R_4$ is determined so as to make the current passing through the resistor $R_4$ be less than that required for holding the thyristor $SCR_3$ "on," when the voltage is supplied to the resistor $R_4$ from the power section 410. The value of the resistor $R_5$ is determined in accordance with the charging time of the capacitor $C_3$.

The capacitance of the capacitor $C_3$ is determined to make the current passing through the thyristor $SCR_1$ invert so that the thyristor $SCR_1$ is turned "off" by a voltage of opposite polarity.

With the arrangement mentioned above, before the shutter release button is depressed, the capacitor $C_3$ is charged in the plorarity shown in FIG. 3 since the thyristors $SCR_1$ and $SCR_3$ are "off,". When a predetermined time has passed after the firing of the tube Xe, or in other words, when the film is sufficiently exposed, the exposure stopping signal B is supplied from the exposure stopping signal generator 406 through the resistor $R_6$ to the thyristor $SCR_3$. Thus, the thyristor $SCR_3$ is turned "on," so that the capacitor $C_3$ is grounded at the electrode connected with the thyristor $SCR_3$. Then, the current passing through the thyristor $SCR_1$ is directed to the capacitor $C_3$, and the thyristor $SCR_1$ is subjected to a voltage of opposite polatiry so that the thyristor $SCR_1$ is turned "off." The capacitor $C_1$ is then gradually charged in the polarity opposite to the one shown in FIG. 3, so that the current is finally prevented from flowing through the tube Xe so that the tube Xe is de-energized.

When the tube Xe is de-energized, the thyristor $SCR_3$ is turned "off" since the resistor $R_4$ has the previously mentioned resistance value. The capacitor $C_3$ is charged in the polarity opposite to the one shown in FIG. 3 when the tube Xe is de-energized but it is thereafter charged in the polarity shown in FIG. 3. The exposure circuit is therefore restored to its original condition.

The focusing control section 500 includes, as shown in FIG. 6, a mark slit image spacing detecting circuit 502, an A/D converter 504, an operating circuit 506, a focusing drive circuit 510, and a focusing motor 512.

The circuit 502 has an input connecting with the separating circuit 202 and the schmidt trigger 304. An output of the circuit 502 is applied to the A/D converter 504.

Figure 9:
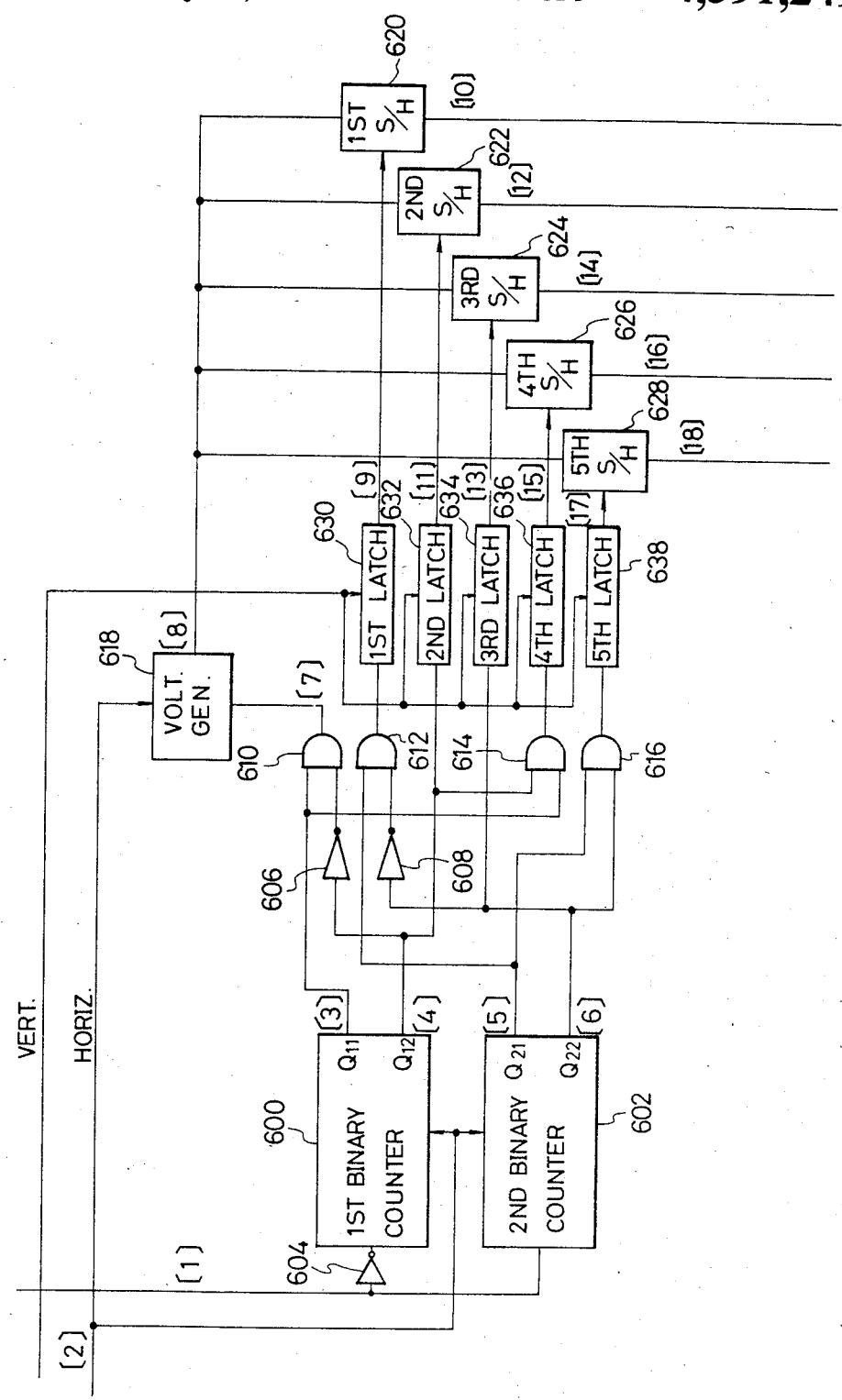
FIG. 9 is a circuit diagram showing a mark image spacing detecting circuit.

As shown in FIG. 9, the circuit 502 includes a first binary counter 600 which counts ends of pulse signals, a second binary counter 602 which counts ends of pulse signals, first through third NOT circuits 604, 606, 608, second through fifth AND circuits 610, 612, 614, 616, a voltage generator 618, first through fifth sample-hold circuits 620, 622, 624, 626, 628 and first through fifth latch circuits 630, 632, 634, 636, 638.

Figure 10:
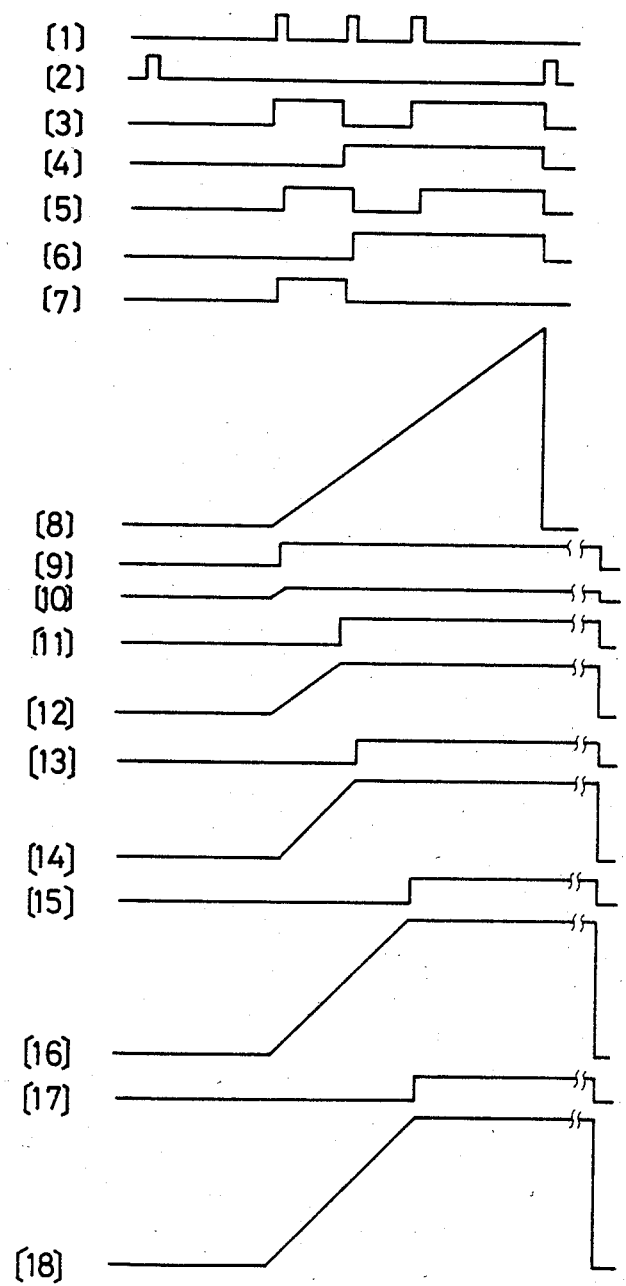
FIG. 10 shows signal patterns in the circuit shown in FIG. 9.

The output signals from the schmidt trigger 304 are shown in FIG. 10(1) and applied through the first NOT circuit 604 to the first binary counter 600. Further, the signals from the schmidt trigger circuit 304 and also applied to the second binary counter 602. The first binary counter 600 counts the ends of the mark slit image signals and produces an output corresponding to the figure of the lowest digit at the output terminal $Q_{11}$ as shown in FIG. 10(3) and an output corresponding to the figure of the highest digit at the output terminal $Q_{12}$ as shown in FIG. 10(4). Similarly, the second binary counter 602 produces outputs as shown in FIGS. 10(5) and (6) at the output terminals $Q_{21}$ and $Q_{22}$, respectively.

The first and second binary counters 600 and 602 are connected with the circuit 202 to receive horizontal synchronous signals therefrom. These signals are used to reset the counters 600 and 602. The second AND circuit 610 has an input terminal which is connected with the terminal $Q_{11}$ of the first binary counter 600 and another input terminal which is connected with terminal $Q_{12}$ through the second NOT circuit 606 which inverts the signal from the terminal $Q_{12}$. The second AND circuit 610 produces an output pulse as shown in FIG. 10(7) which starts at the start of the first mark slit image signal. The output of the AND circuit 610 is applied to the voltage generator 618 as the voltage start timing signal.

The voltage generator 618 has a latch function and starts to produce a linearly increasing voltage signal as shown in FIG. 10(8) at the start of the first mark slit image signal. The output of the voltage generator 618 is applied to the first through fifth sample-hold circuits 620, 622, 624, 626 and 628. The voltage generator 618 is connected to receive horizontal synchronous signals as shown in FIG. 10(2) from the circuit 202 and the generation of the voltage signal is terminated when the horizontal synchronous signal is received.

The first through fifth latch circuits 630 through 638 produce timing signals respectively for the first through fifth sample-hold circuits 620 through 628. The latch circuits 630 through 638 are connected to receive vertical synchronous signals as release signals and the circuits therefore continue to provide latching function until the vertical synchronous signal is received.

The third AND circuit 612 has an input terminal connected with the output terminal $Q_{21}$ of the second binary counter 602 and another input terminal connected with the output terminal $A_{22}$ through the third NOT circuit 608. The output of the third AND circuit 612 is applied to the first latch circuit 630 which produces a signal as shown in FIG. 10(9). The output of the latch circuit 630 is applied to the first sample-hold circuit 620 as the timing signal. As noted in FIG. 10, the timing signal to the circuit 620 starts at the end of the first mark slit image signal. The first sample-hold circuit 620 holds the input signal when a high level timing signal is received from the latch circuit 630 so that it maintains the voltage signal from the generator 618 at the end of the first mark slit image signal as shown in FIG. 10(10).

The second latch circuit 632 has an input connected with the input terminal $Q_{12}$ of the first binary counter 600 to receive the signal as shown in FIG. 10(4) and produce a timing signal which is shown in FIG. 10(11) and applied to the second sample-hold circuit 622. The timing signal starts at the start of the second mark slit image signal. The second sample-hold circuit 622 holds the input signal when a high level timing signal is received so that it produces an output which is shown in FIG. 10(12) and correspond to the voltage signal as produced by the generator 618 in the period between the start of the first mark slit image signal and the start of the second mark slit image signal.

The third latch circuit 634 has an input terminal connected with the output terminal $Q_{22}$ of the second binary counter 602 to receive a signal which is shown in FIG. 10(6) and starts at the end of the second mark slit image signal. The third latch circuit 634 produces a timing signal which is shown in FIG. 10(13) and applied to the sample-hold circuit 624. Thus, it will be understood that the third sample-hold circuit 614 produces a signal which corresponds to the voltage signal as produced by the generator 618 in a period between the start of the first mark slit image signal and the end of the second mark slit image signal as shown in FIG. 10(14).

The fourth latch circuit 636 has an input connected with the output of the fourth AND circuit 614 which has inputs connected respectively with the input terminals $Q_{11}$ and $Q_{12}$ of the first binary counter 600. The fourth latch circuit 636 therefore produces a timing signal which starts at the start of the third mark slit image as shown in FIG. 10(15) and applied to the fourth sample-hold circuit 626. Thus, the fourth sample-hold circuit 626 produces an output which corresponds to the voltage signal as produced by the generator 618 in a period between the start of the first mark slit image signal and the start of the third mark slit image signal as shown in FIG. 10(16).

The fifth latch circuit 638 has an input converted with the output of the fifth AND circuit 616 which has inputs connected respectively with the output terminals $Q_{21}$ and $Q_{22}$ of the second binary counter 602. Thus, the fifth latch circuit 638 produces a timing signal which starts at the end of the third mark slit image signal as shown in FIG. 10(17). The timing signal is applied to the fifth sample-hold circuit 628 which produces an output corresponding to the voltage signal as produced by the generator 618 in the period between the start of the first mark slit image signal and the end of the third mark slit image signal as shown in FIG. 10(18).

The output signals of the sample-hold circuits 620 through 628 are maintained until a vertical synchronous signal is received from the circuit 202 since they receive timing signals from the latch circuits 630 through 638 so that a sufficient time is provided for the operation of the A/D converter 504.

The output signals of the first through fifth sample-hold circuits 620, 622, 624, 626 and 628 are applied to the A/D converter 504 which converts the input signals into digital signals. The outputs of the A/D converter 504 is connected with the operation circuit 506.

The operation circuit 506 receives the signals of the mark slit image counter 206 of timing signal section 200 and of the A/D converter 504 and produces a focus control signal adapted to be applied through the focusing drive circuit 510 to the focusing motor 512.

Figure 11:
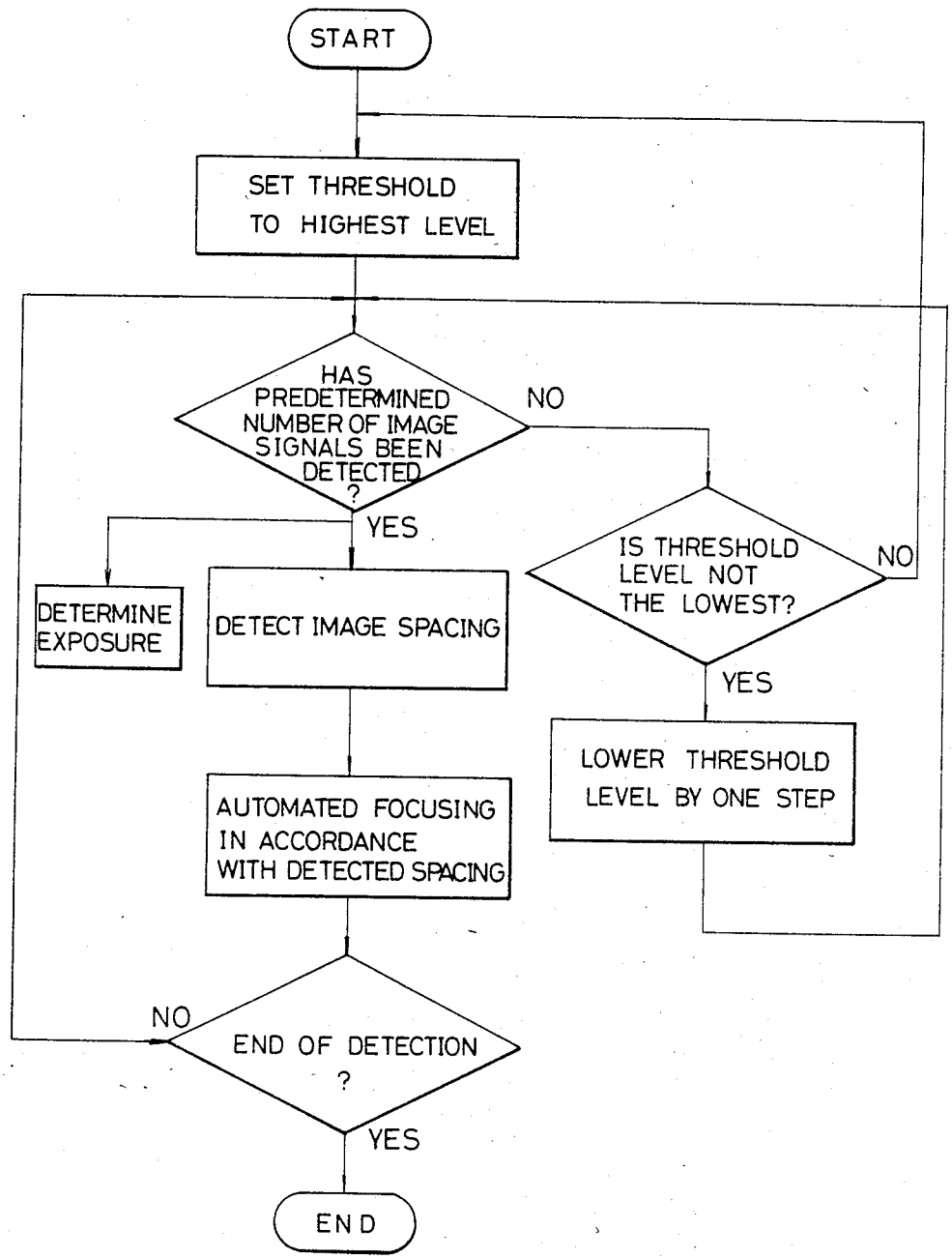
FIG. 11 is a flow chart of exposure control and focusing.

Referring now to FIG. 11 which shows a flow chart of the operation of the focusing and the exposure time determining, the output of the circuit 506 at first adjusts the TL changing means 306 so that the highest value $V_{T1}$ of the threshold level is produced. Then, the number of the mark slit image signals is obtained by the signal from the counter 206. In the counter 206, a judgement is made as to whether the predetermined number, for example, three of the image signals are detected. If the predetermined number of slit image signals are not detected, the circuit 504 produces a signal bases on the signal from the counter 206 for controlling the TL changing means 306 to decrease the level by one step. If the threshold level is the lowest, the level is returned to the highest value. The procedure is repeated until the counter 206 detects the predetermined number of mark slit image signals.

When the predetermined number of image signals are detected, the circuit 506 applies a high level signal to the spacing detecting circuit 502 so that the spacing detecting circuit 502 starts to operate. The circuit 506 also applies a high level signal to the TL changing means 306 so that the threshold level TL at this time is applied to the compensating means 402 and the exposure stopping signal generator 406 determines the exposure time. The voltage signals from the first through fifth sample-hold circuits 620, 622, 624, 626 and 628 are converted by the A/D converter 504 into digital signals DA, DB, DC, DD, DE, respectively, and applied to the operation circuit 506. The operation circuit 506 performs calculations to obtain the spacings l1, l2 and Δl based on the equations:

$$l1 = \frac{DB + DC - DA}{2}$$

$$l2 = \frac{DD + DE - DB - DC}{2}$$

$$\Delta l = l1 - l2$$

Then, the circuit 506 produces an output corresponding to the vaue Δl and applies it to the focusing drive circuit 510 to thereby produce a focusing motor drive current. The amount of focus control is determined by the value Δl whereas the direction of the control depends on whether the value Δl is positive or negative.

The invention has thus been shown and described with reference to a specific embodiment, however, it should be noted that the invention is in no way limited to the details of the illustrated arrangements but changes and modifications may be made without departing from the scope of the appended claims.

We claim:

1. An ophthalmic photographing apparatus comprising an illuminating optical system for projecting beams of illuminating light to a subject to be photographed, a mark projecting optical system for projecting, together with the beams of illuminating light, a mark on the subject by a mark projecting light, a photographing optical system including a photographing film plane and optical means for producing an image of the subject on the film plane, photodetecting means for detecting a light which is a reflection of the mark projecting light at the retina to produce a mark signal, exposure control means including photographing light source means and means for controlling the light source means in accordance with the mark signal to control quantity of photographing light incident to the film plane so that a correct exposure is accomplished in photographing.

2. An apparatus in accordance with claim 1 in which said illuminating optical system is of a type in which intensity of the projecting beams can be variably adjusted.

3. An apparatus in accordance with claim 2 which further includes second photodetecting means for detecting intensity of the illuminating light and compensating means for modifying said mark signal in accordance with output of said photodetecting means.

4. An apparatus in accordance with claim 2 which further includes an observing optical system for observing said subject which is being illuminated by the illuminating light second, photodetecting means for detecting intensity of the illuminating light and compensating means for modifying said mark signal in accordance with output of said second photodetecting means whereby the mark signal is modified so that it represents reflectivity of the subject to be photographed.

5. An apparatus in accordance with claim 1 in which the last mentioned means includes means for controlling the photographing light source means so that quantity of light projected from the photographing light source means is decreased in response to an increase in the mark signal.

6. An apparatus in accordance with claim 1 in which said mark projecting optical system is a focusing mark projecting system.

7. An apparatus in accordance with claim 1 which further includes photodetecting means for detecting intensity of the mark projecting light to produce a projecting light signal, said exposure control means including compensating means for modifying said mark signal in accordance with the projecting light signal so that the mark signal is decreased in response to an increase in the projecting light signal.

8. An ophthalmic photographing apparatus comprising an observing light projecting section for projecting light beams having different intensities to an object to be photographed for an observation of said object, a photographing light projecting section for projecting beams of photographing illumination light for photographing, a photographing section including a photographing film plane and focusing lens means for producing an image of the object to be photographed on the film plane, a photodetecting section for detecting a light from said observing light projecting section reflected at an area which is projected with the light beams of stronger intensity than the light beams being projected to other areas to produce a reflection light signal, and an exposure control section for controlling quantity of photographing light incident to the film plane in accordance with the reflection light signal so that a correct exposure is accomplished in photographing.

9. An apparatus in accordance with claim 8 in which said light projecting section includes illuminating means for illuminating the object to be photographed by an illuminating light and focusing mark projecting means for projecting a focusing mark on said object to be photographed by a mark projecting light which is stronger than the illuminating light so as to form on the object a projected image of the focusing mark of which location depends on focusing condition of the focusing lens means, said photodetecting section including means for detecting the location of the focusing mark to produce a mark location signal, focusing means being provided for controlling said focusing lens means in accordance with said mark location signal.

10. An apparatus in accordance with claim 9 in which said photodetecting section includes means for detecting intensity of the projected image of the focusing mark to produce the reflection light signal.

11. An apparatus in accordance with claim 9 which includes means for detecting intensity of the mark projecting light and means for modifying the reflection light signal in accordance with the intensity of the mark projecting light.

12. An apparatus in accordance with claim 9 which includes means for detecting intensity of the illuminating light and intensity of the mark projecting light, and means for modifying the reflection light signal in accordance with the intensities of the illuminating light and the mark projecting light.

* * * * *